United States Patent [19]

Appel et al.

[11] Patent Number: 5,534,634
[45] Date of Patent: Jul. 9, 1996

[54] PROCESS FOR PREPARING TRIFLUOROETHYL SULFUR COMPOUNDS FROM THIOLATES AND 1-CHLORO-2,2,2-TRIFLUOROETHANE

[75] Inventors: Wolfgang Appel, Kelkheim; Frank Ebmeyer, Hattersheim; Tobias Metzenthin, Frankfurt; Günter Siegemund, Hofheim, all of Germany

[73] Assignee: Hoechst AG, Germany

[21] Appl. No.: 314,943

[22] Filed: Sep. 29, 1994

[30] Foreign Application Priority Data

Sep. 29, 1993 [DE] Germany .................... 43 33 058.4

[51] Int. Cl.$^6$ ...................... C07D 213/70; C07D 277/72; C07D 235/28; C07C 321/14
[52] U.S. Cl. .................... 546/303; 548/165; 548/182; 548/221; 548/229; 548/306.4; 548/343.1; 562/432; 568/56; 568/59
[58] Field of Search .................... 546/303; 548/165, 548/221, 306.4, 343.1, 182, 229; 568/56, 59; 562/432

[56] References Cited

U.S. PATENT DOCUMENTS 5,258,547  11/1993  Sheldrake ................. 560/226

FOREIGN PATENT DOCUMENTS 2251618  7/1992  United Kingdom ............... 560/228

OTHER PUBLICATIONS

J. Chem. Soc. Perkin Trans., "Syntheses and Thermal Behaviour of 9–Substituted 9–Thia–10–azaphenanthrenes" (1991), pp. 1733–1747.
Tetrahedron 48, "On the Reacttivity of $CF_nH_{3-n}CH_2X$ (n = 0, 1, 2, and 3 and X = H or Halogen atom)" (1992), pp. 5823–5830.
J. Fluorine Chem. 31, "1,1–Dihydroperfluoroalkylations of Nucleophiles with (1,1–Dihydroperfluoroalkyl)phenyliodonium Triflates" (1986), pp. 231–236.
J. Fluorine Chem. 31, "1,1–Dihydroperfluoroalkylations of Nucleophiles with (1,1–Bulletin Chem. Soc. Japan 50,) A Convenient Preparation of Arylthioynamines", pp. 3069–3070 (1986).

Primary Examiner—Alan L. Rotman
Attorney, Agent, or Firm—Connolly & Hutz

[57] ABSTRACT

Process for preparing trifluoroethyl sulfur compounds from thiolates and 1-chloro-2,2,2-trifluoroethane. The invention relates to the preparation of trifluoroethyl sulfur compounds of the formula $RSCH_2CF_3$ by reacting 1-chloro-2,2,2-trifluoroethane $CH_2Cl—CF_3$ in a polar aprotic solvent with salts of thiols of the formula RSH, where R can be an alkyl or aryl radical or a heterocyclic radical.

16 Claims, No Drawings

PROCESS FOR PREPARING TRIFLUOROETHYL SULFUR COMPOUNDS FROM THIOLATES AND 1-CHLORO-2,2,2-TRIFLUOROETHANE

DESCRIPTION

Process for preparing trifluoroethyl sulfur compounds from thiolates and 1-chloro-2,2,2-trifluoroethane The thiolates, which are known to be very nucleophilic, have hitherto been able to be alkylated using the industrially readily available 1-chloro-2,2,2-trifluoroethane (hereinafter abbreviated as chlorotrifluoroethane or R133a) in only two exceptional cases. Thus, R133a was reacted with an aqueous solution of benzyl mercaptan to give benzyl trifluoroethyl thioether (GB-A-2,251,618, example 3). However, this reaction is carried out under pressure in a bomb tube and requires the use of a phase transfer catalyst. In another publication, mention is only made of the reaction with an intermediately produced biphenyl, namely 2-(2'-aminophenyl)thiophenol (H. Shimizu et al., J. Chem. Soc. Perkin Trans. 1, 1991, 1733–1747; table 1, compound 3 v). However, the experimental description on page 1741 illustrates the alkylation of the sulfur function only for the example of the reactive methyliodide and does not consider the known low reactivity of R133a. It has generally been expected that compounds of the type $CF_3CH_2X$ are extremely unreactive as alkylation agents (N. Bodor et al., Tetrahedron 48 [1992] 5823–5830 and T. Umemoto, Y. Gotoh, J. Fluorine Chem. 31 [1986] 231–236).

It has now surprisingly been found that chlorotrifluoroethane can nevertheless be reacted in a polar and aprotic solvent with aliphatic, aromatic and heterocyclic thiolates to give good yields. A catalyst is here not required. In addition, the reaction can be carried out at a low pressure of up to 5 bar (simple closed apparatus) or even completely without applied pressure (atmospheric pressure).

The present invention accordingly provides a process for preparing trifluoroethyl sulfur compounds from thiolates and 1-chloro-2,2,2-trifluoroethane, which comprises allowing 1-chloro-2,2,2-trifluoroethane to act in a polar aprotic solvent upon salts of thiols of the formula RSH, where R is an unsubstituted or substituted radical as defined below:
$C_1$–$C_{20}$-alkyl
or $C_3$–$C_{12}$-cycloalkyl
or a monocyclic, condensed dicyclic or condensed tricyclic aryl radical,
or a saturated or unsaturated monocyclic or dicyclic heterocyclic radical, which contains a total of one or two heteroatoms, which can, independently of one another, he N, S or O.

The reaction is preferably carried out under atmospheric pressure (open apparatus) or under a pressure of up to 5 bar (simple closed apparatus). Higher pressure, e.g. from 5 to 10 bar, is also possible without problems, but is not necessary.

The trifluoroethyl sulfur compounds prepared have the formula $RSCH_2CF_3$.

The reaction is generally carried out at temperatures of from 0° to 100° C.; a higher reaction temperature is possible but offers no advantages. The reaction is preferably carried out at temperatures of from 20° to 70° C., in particular at from 40° to 60° C. The chlorotrifluoroethane is preferably used in excess to accelerate the reaction and to increase the yields. Unconsumed chlorotrifluoroethane can be recovered by distillation after the reaction.

Suitable polar aprotic solvents are, for example, N-methylpyrrolidone, N-methylformamide, dimethylformamide, dimethylacetamide, sulfolane, dimethyl sulfoxide, butyrolactone and tetrahydrofuran. Of these solvents, preference is given to using N-methylformamide, dimethylformamide, dimethylacetamide, dimethyl sulfoxide and butyrolactone, in particular N-methylpyrrolidone and dimethylformamide.

When using thiolates having further functional groups, the reaction occurs exclusively at the sulfur function, while, for example, nitrogen or carboxylate functions which are likewise nucleophilic are not attacked.

Suitable thiolates are all usual salts of the specified thiols of the formula RSH.

In general, R is as defined below:
$C_1$–$C_{20}$-alkyl,
unsubstituted or substituted by one or two radicals selected from the group consisting of amino, F, $C_1$–$C_3$-alkylamino, $C_1$–$C_3$-dialkylamino, hydroxyl, carboxyl, $C_1$–$C_6$-alkoxy, $C_3$–$C_{12}$-cycloalkyl, pyridyl, imidazolyl, thiazolyl, oxazolyl, phenyl, with phenyl being unsubstituted or substituted by one or two radicals selected from the group consisting of F, Cl, Br, amino, $C_1$–$C_3$-alkylamino, $C_1$–$C_3$-dialkylamino, hydroxyl, carboxyl, $C_1$–$C_3$-alkoxy, $C_1$–$C_6$-alkyl;
or $C_3$–$C_{12}$-cycloalkyl,
unsubstituted or substituted by one or two radicals selected from the group consisting of $C_1$–$C_6$-alkyl, F, amino, $C_1$–$C_3$-alkylamino, $C_1$–$C_3$-dialkylamino, hydroxyl, carboxyl, $C_1$–$C_6$-alkoxy, pyridyl, imidazolyl, thiazolyl, oxazolyl, phenyl, with phenyl being unsubstituted or substituted by one or two radicals selected from the group consisting of F, Cl, Br, amino, $C_1$–$C_3$-alkylamino, $C_1$–$C_3$-dialkylamino, hydroxyl, carboxyl, $C_1$–$C_3$-alkoxy, $C_1$–$C_6$-alkyl;
or a monocyclic, condensed dicyclic or condensed tricyclic aryl radical,
unsubstituted or substituted by one or two radicals selected from the group consisting of $C_1$–$C_{56}$-alkyl, F, Cl, Br, amino, $C_1$–$C_3$-alkylamino, $C_1$–$C_3$-dialkylamino, hydroxyl, carboxyl, $C_1$–$C_6$-alkoxy;
or a saturated or unsaturated, monocyclic or dicyclic heterocyclic radical, which contains a total of one or two heteroatoms, which can, independently of one another, be N, S or O,
where the radical is unsubstituted or substituted by one or two radicals selected from the group consisting of $C_1$–$C_6$-alkyl, F, amino, $C_1$–$C_3$-alkylamino, $C_1$–$C_3$-dialkylamino, hydroxyl, carboxyl, $C_1$–$C_6$-alkoxy, and also, if the heterocyclic radical is aromatic, Cl and Br.

"$C_1$–$C_3$-dialkylamino" is here an amino group substituted by one or two alkyl radicals, with the two alkyl radicals having, independently of one another, from 1 to 3 carbon atoms.

Preferably, R is as defined below:
$C_1$–$C_{12}$-alkyl,
unsubstituted or substituted by one or two radicals selected from the group consisting of F, amino, $C_1$–$C_3$-alkylamino, $C_1$–$C_3$-dialkylamino, hydroxyl, carboxyl, $C_1\infty C_3$-alkoxy, $C_3$–$C_8$-cycloalkyl, pyridyl, imidazolyl, thiazolyl, oxazolyl, phenyl, with phenyl being unsubstituted or substituted by one or two radicals selected from the group consisting of F, Cl, Br, amino, $C_1$–$C_3$-alkylamino, $C_1$–$C_3$-dialkylamino, hydroxyl, carboxyl, $C_1$–$C_3$-alkoxy, $C_1$–$C_4$-alkyl;
or $C_3$–$C_8$- cycloalkyl, unsubstituted or substituted by one or two radicals selected from the group consisting of $C_1$–$C_4$-alkyl, F, amino, $C_1$–$C_3$-alkylamino, $C_1$–$C_3$-dialkylamino, hydroxyl, carboxyl, $C_1$–$C_3$-alkoxy, pyridyl, imidazolyl, thiazolyl, oxazolyl, phenyl, with phenyl being unsubstituted or substituted by one or two radicals selected from the group consisting of F, Cl, Br, amino, $C_1$–$C_3$-alkylamino, $C_1$–$C_3$-dialkylamino, hydroxyl, carboxyl, $C_1$–$C_3$-alkoxy, $C_1$–$C_4$-alkyl;

or a monocyclic, condensed dicyclic or condensed tricyclic aryl radical, unsubstituted or substituted by one or two radicals selected from the group consisting of $C_1$–$C_4$-alkyl, F, Cl, Br, amino, $C_1$–$C_3$-alkylamino, $C_1$–$C_3$-dialkylamino, hydroxyl, carboxyl, $C_1$–$C_3$-alkoxy;

or a saturated or unsaturated, monocyclic or dicyclic heterocyclic radical, which contains a total of one or two heteroatoms, which can, independently of one another, be N, S or O, where the radical is unsubstituted or substituted by one or two radicals selected from the group consisting of $C_1$–$C_4$-alkyl, F, amino, $C_1$–$C_3$-alkylamino, $C_1$–$C_3$-dialkylamino, hydroxyl, carboxyl, $C_1$–$C_3$-alkoxy, and also, if the heterocyclic radical is aromatic, Cl and Br.

In particular, R is as defined below:

$C_1$–$C_6$-alkyl, unsubstituted or substituted by one or two radicals selected from the group consisting of F, amino, $C_1$–$C_3$-alkylamino, $C_1$–$C_3$-dialkylamino, hydroxyl, carboxyl, $C_1$–$C_3$-alkoxy, $C_3$–$C_8$-cycloalkyl, pyridyl, imidazolyl, thiazolyl, oxazolyl, phenyl, with phenyl being unsubstituted or substituted by one or two radicals selected from the group consisting of F, Cl, Br, $C_1$–$C_3$-alkyl, $C_1$–$C_3$-alkoxy;

or $C_3$–$C_6$-cycloalkyl, unsubstituted or substituted by one or two radicals selected from the group consisting of $C_1$–$C_4$-alkyl, F, amino, $C_1$–$C_3$-alkylamino, $C_1$–$C_3$-dialkylamino, hydroxyl, carboxyl, $C_1$–$C_3$-alkoxy, pyridyl, imidazolyl, thiazolyl, oxazolyl, phenyl;

or phenyl, unsubstituted or substituted by one or two radicals selected from the group consisting of $C_1$–$C_3$-alkyl, F, Cl, Br, amino, $C_1$–$C_3$-alkylamino, $C_1$–$C_3$-dialkylamino, hydroxyl, carboxyl, $C_1$–$C_3$-alkoxy;

or an unsaturated monocyclic or dicyclic heterocyclic radical, which contains a total of one or two heteroatoms, which can, independently of one another, be N, S or O, where the radical is unsubstituted or substituted by one or two radicals selected from the group consisting of $C_1$–$C_3$-alkyl, F, amino, $C_1$–$C_3$-alkylamino, $C_1$–$C_3$-dialkylamino, hydroxyl, carboxyl, $C_1$–$C_3$-alkoxy, and also, if the heterocyclic radical is aromatic, Cl and Br.

Most preferably, R is as defined below:

$C_1$–$C_4$-alkyl;

or $C_3$$C_6$-cycloalkyl;

or phenyl, unsubstituted or substituted by one or two radicals selected from the group consisting of methyl, F, Cl, Br, amino, $C_1$–$C_3$-alkylamino, $C_1$–$C_3$-dialkylamino, hydroxyl, carboxyl, methoxy;

or pyridyl, imidazolyl, benzimidazolyl, thiazolyl, benzothiazolyl, oxazolyl or benzoxazolyl.

The thiolates to be used in the process of the invention can generally be produced by action of equimolar amounts of various monobasic or dibasic organic or inorganic bases, such as, for example, alkali metal, alkaline earth metal, ammonium or alkylammonium hydroxide, sodium hydride, calcium hydride, alkali metal or alkaline earth metal alkoxide, ammonia, primary, secondary or tertiary alkylamines, arylamines or aralkylamines, amidines or pyridine, on the corresponding thiol. The base used is preferably sodium hydroxide, potassium hydroxide, pyridine, ammonia, primary to tertiary alkylamines and aralkylamines or sodium hydride. In particular, sodium hydroxide, potassium hydroxide, sodium hydride or alkylamines are used. Good results can here be achieved either under anhydrous reaction conditions or, for example, using aqueous alkali metal hydroxide solution. The thiolate can be prepared prior to the reaction or can be produced in situ. Suitable cations for the thiolate used are accordingly, for example: $Na^+$, $K^+$, $Ca^{2+}$, $NR^1R^2R^+$ ($R^{1-3}$ =$C_1$–$C_6$-n-alkyl, $C_1$–$C_6$-cycloalkyl, aryl, H), $C_5H_5NH^+$ (pyridinium), $C_6H_{12}N_2H^+$ (cation of the amidine diazabicyclononene, DBN); preferably $Na^+$, $K^+$, $NR^1R^2R^3H^+$ ($R^{1-3}$=$C_1$–$C_6$-n-alkyl, $C_1$–$C_6$-cycloalky aryl, H), $C_5H_5NH^+$; in particular $Na^+$, $K^+$, $NR^1R^2R^3H^+$ ($R^{1-3}$= $C_1$–$C_6$-n-alkyl, aryl, H), $C_5H_5NH^+$.

The thiols on which the thiolates are based can generally be prepared by heating hydrogen sulfide or its metal salts with organic halogen compounds, with the halogen function being replaced by the mercapto group.

Depending on the cation of the thiolate used (counterion), the reaction with the chlorotrifluoroethane (R133a) forms the corresponding monovalent or divalent metal, ammonium or alkylammonium chloride as the only by-product from which the desired trifluoroethyl sulfur compounds can easily be separated (e.g. by filtration). An advantage of the process of the invention is therefore that there is no formation of iodine-containing or bromine-containing salts, the disposal of which is difficult.

Suitable materials of construction for the reaction vessel are all sufficiently inert materials such as, for example, unalloyed steel, nickel, Hastelloy, and also glass.

The method of the invention for preparing trifluoroethyl sulfur compounds saves costs, since it is a single-vessel process which can be carried out at atmospheric pressure or under a low applied pressure and in a single stage. The compounds prepared can be used as intermediates and end products of active ingredients for crop protection and pharmaceuticals.

A suitable procedure for preparing the trifluoroethyl sulfur compounds comprises initially charging the thiol selected in a suitable solvent under inert gas and converting it into the thiolate using alkali metal hydroxide. The required amount of chlorotrifluoroethane is subsequently passed into the solution at room temperature from a reservoir and the mixture is then heated to the reaction temperature. The progress of the reaction can be seen from the formation of alkali metal chloride or be monitored by thin-layer chromatography. Depending on the reactivity of the thiolate used, the reaction is complete after 3–12 hours. The reaction mixture is poured into water and the mixture is extracted with an inert organic solvent. The organic phase is subsequently dried and the pure product is isolated by means of distillation or filtration.

EXAMPLE 1

In a 2-necked flask having a dry ice condenser fitted on top, 250 ml of dimethylformamide and 93.8 g of a 50% strength by weight aqueous sodium hydroxide solution were mixed and the oxygen was largely displaced by passing in argon. 122 g of thiophenol were subsequently added and 130 g of chlorotrifluoroethane (R133a) were passed into the reaction mixture at a temperature of about 60° C. The reaction was complete after 16 hours (TLC analysis: silica gel, dichloromethane). The reaction mixture was poured into water, the mixture was extracted three times with dichloromethane and the combined organic extracts were dried over sodium sulfate. The solvent was subsequently distilled off and the oily residue was distilled in vacuo (68° C./16 mbar); this gave 134.5 g of 2,2,2-trifluoroethylthiobenzene.

EXAMPLE 2

11.1 g of 2-mercaptopyridine were initially charged in 60 ml of dry dimethylformamide and slowly admixed with 4 g of a 60% strength by weight suspension of sodium hydride in paraffin. The solution was subsequently cooled to 0° C. and 12 g of chlorotrifluoroethane were passed in. The reaction mixture was transferred to a stirred autoclave and heated at 100° C. for 12 hours. A maximum pressure of 2.5 bar was established. The cooled reaction mixture was subsequently poured into water and extracted three times with dichloromethane. The solvent was distilled off from the organic phase dried with $Na_2SO_4$ and the residue was fractionated in vacuo (78° C./9.5 mbar). This gave 8.0 g of 2-(2',2',2'-trifluoroethylthio) pyridine as a colorless oil.

EXAMPLE 3

A two-necked flask was charged under nitrogen with 45 ml of dimethylformamide and 16 g of a 50% strength by weight aqueous sodium hydroxide solution. After addition of 15 g of 2-mercaptobenzoic acid, 18 g of chlorotrifluoroethane were passed in at 0° C. and the reaction mixture was then transferred into a stirred autoclave. The mixture was heated at 100° C. for 12 hours (maximum pressure: 2.5 bar), allowed to cool and the crude product was then precipitated by addition of concentrated hydrochloric acid. The dried crude product was recrystallized from hot formic acid, giving 5.3 g of 2-(2',2',2'-trifluoroethylthio)benzoic acid having a melting point of 226°–227° C.

EXAMPLE 4

A two-necked flask having a dry ice condenser fitted on top was charged with 50 ml of dry dimethylformamide and 2 g of a 60% strength by weight suspension of sodium hydride in paraffin, and subsequently 7.3 g of 4-chlorothiophenol in 10 ml of dimethylformamide were added dropwise. Chlorotrifluoroethane was then passed in at a reaction temperature of about 60° C., until the gas began to condense in the dry ice condenser. The mixture was stirred for a further 5 hours and the course of the reaction was monitored by thin-layer chromatography (silica gel; ethyl acetate/petroleum ether 1/5). The reaction mixture was worked up by pouring into water and extracting with dichloromethane. The combined organic extracts were dried and the solvent was distilled off at reduced pressure. The oily residue was subsequently distilled (43°–45° C./0.1 mbar), giving 8.8 g of 4-chloro( 2',2',2'-trifluoroethylthio)benzene

EXAMPLE 5

A two-necked flask having a dry ice condenser fitted on top was charged under argon with 65 ml of dimethylformamide and 16 g of a 50% strength by weight sodium hydroxide solution, and subsequently 25 g of 4-aminothiophenol were added. 35 g of chlorotrifluoroethane were subsequently passed into the clear solution heated to 60° C. The course of the reaction was monitored by thin-layer chromatography (silica gel; dichloromethane) and after about 3 hours the reaction mixture was poured into water. The mixture was extracted with dichloromethane, the combined organic extracts were dried with $Na_2SO_4$ and the reaction product was precipitated as hydrochloride by passing in hydrogen chloride. The precipitate was recrystallized from ethyl acetate and this gave 28 g of pure 4-amino-(2',2',2'-trifluoroethylthio)benzene (HCl adduct) having a melting point of 230°–231° C. (decomposition).

EXAMPLE 6

In an apparatus as in Example 5, 13 g of p-methylthiophenol were deprotonated with 4 g of sodium hydride (60% strength by weight suspension in paraffin) in 90 ml of dry dimethylformamide. The reaction mixture was subsequently heated to 60° C. and 23 g of chlorotrifluoroethane were passed in while stirring. After stirring for 5.5 hours at 50°–60° C., the reaction mixture was poured into water and extracted three times with dichloromethane. The organic phase was additionally washed with water and saturated sodium hydrogen carbonate solution and then dried over sodium sulfate. The solvent was distilled off under reduced pressure and the residue was fractionated (49°–51° C./1 mbar). This gave 13.4 g of 4-methyl-(2',2',2'-trifluoroethylthio)benzene as a colorless oil.

EXAMPLE 7

2 g of sodium hydride were suspended in 40 ml of dimethylformamide, and 8.4 g of 2-mercaptobenzothiazole in 20 ml of dimethylformamide were added dropwise at 0° C. After 30 minutes, 12 g of R133a were passed in at the same temperature. The solution was transferred to a stirred autoclave and heated at 100° C. for 18 hours. A maximum pressure of 2.1 bar was established. The cooled reaction mixture was subsequently poured into water and extracted three times with dichloromethane. The solvent was distilled off from the organic phase dried with $Na_2SO_4$ and the residue was fractionated in vacuo (80° C./0.05 mbar). This gave 5.1 g of 2-(2',2',2'-trifluoroethylthio)benzothiazole.

EXAMPLE 8

A two-necked flask was charged under nitrogen with 150 ml of dimethylformamide and 40 g of a 50% strength by weight sodium hydroxide solution. After slow addition of 62 g of benzyl mercaptan, the reaction solution was allowed to again cool to 30° C. and 80 g of chlorotrifluoroethane were then passed in. After 0.5 h, the reaction temperature was raised to 60° C. and the course of the reaction was monitored by thin-layer chromatography (silica gel; petroleum ether/dichloromethane 1/1). After 3 hours, the mixture was allowed to cool to room temperature and the contents of the flask were then poured into about 200 ml of water. The mixture was extracted three times with dichloromethane and the combined organic extracts were washed three times with water and once with saturated sodium chloride solution. After drying over sodium sulfate, the solvent was distilled off under reduced pressure and the residue was distilled in vacuo (57° C./1.5 mbar). This gave 92 g of 2,2,2-trifluoroethyl benzyl sulfide as a colorless oil.

What is claimed is:

1. A process for preparing trifluoroethyl sulfur compounds from thiolates and 1-chloro- 2,2,2-trifluoroethane, which consists essentially of allowing 1-chloro-2,2,2-trifluoroethane to act in a polar aprotic solvent upon salts of thiols of the formula RSH, at a low pressure of up to 5 bar, where R is an unsubstituted or substituted radical as defined below:

$C_1$–$C_{20}$-alkyl or $C_3$—$C_{12}$-cycloalkyl or a monocyclic, condensed dicyclic or condensed tricyclic aryl radical, or a saturated or unsaturated monocyclic or dicyclic heterocyclic radical, which contains a total of one or two heteroatoms, which can, independently of one another, be N, S or O.

2. The process as claimed in claim 1, wherein R is as defined below:

$C_1$–$C_{20}$-alkyl,
unsubstituted or substituted by one or two radicals selected from the group consisting of amino, F, $C_1$–$C_3$-alkylamino, $C_1$–$C_3$-dialkylamino, hydroxyl, carboxyl, $C_1$–$C_6$-alkoxy, $C_3$–$C_{12}$-cycloalkyl, pyridyl, imidazolyl, thiazolyl, oxazolyl, phenyl, with phenyl being unsubstituted or substituted by one or two radicals selected from the group consisting of F, Cl, Br, amino, $C_1$–$C_3$-alkylamino, $C_1$–$C_3$-dialkylamino, hydroxyl, carboxyl, $C_1$–$C_3$-alkoxy, $C_1$–$C_6$-alkyl;

or $C_3$–$C_{12}$-cycloalkyl,
unsubstituted or substituted by one or two radicals selected from the group consisting of $C_1$–$C_6$-alkyl, F, amino, $C_1$–$C_3$-alkylamino, $C_1$–$C_3$-dialkylamino, hydroxyl, carboxyl, $C_1$–$C_6$-alkoxy, pyridyl, imidazolyl, thiazolyl, oxazolyl, phenyl, with phenyl being unsubstituted or substituted by one or two radicals selected from the group consisting of F, Cl, Br, amino, $C_1$–$C_3$-alkylamino, $C_1$–$C_3$-dialkylamino, hydroxyl, carboxyl, $C_1$–$C_3$-alkoxy, $C_1$–$C_6$-alkyl;

or a monocyclic, condensed dicyclic or condensed tricyclic aryl radical,
unsubstituted or substituted by one or two radicals selected from the group consisting of $C_1$–$C_6$-alkyl, F, Cl, Br, amino, $C_1$–$C_3$-alkylamino, $C_1$–$C_3$-dialkylamino, hydroxyl, carboxyl, $C_1$–$C_6$-alkoxy;

or a saturated or unsaturated, monocyclic or dicyclic heterocyclic radical, which contains a total of one or two heteroatoms, which can, independently of one another, be N, S or O,
where the radical is unsubstituted or substituted by one or two radicals selected from the group consisting of $C_1$–$C_6$-alkyl, F, amino, $C_1$–$C_3$-alkylamino, $C_1$–$C_3$–dialkylamino, hydroxyl, carboxyl, $C_1$–$C_6$-alkoxy, and also, if the heterocyclic radical is aromatic, Cl and Br.

3. The process as claimed in claim 1, wherein R is as defined below:

$C_1$–$C_{12}$-alkyl,
unsubstituted or substituted by one or two radicals selected from the group consisting of F, amino, $C_1$–$C_3$-alkylamino, $C_1$–$C_3$-dialkylamino, hydroxyl, carboxyl, $C_1$–$C_3$-alkoxy, $C_3$–$C_8$-cycloalkyl, pyridyl, imidazolyl, thiazolyl, oxazolyl, phenyl, with phenyl being unsubstituted or substituted by one or two radicals selected from the group consisting of F, Cl, Br, amino, $C_1$–$C_3$-alkylamino, $C_1$–$C_3$-dialkylamino, hydroxyl, carboxyl, $C_1$–$C_3$-alkoxy, $C_1$–$C_4$-alkyl;

or $C_3$–$C_8$-cycloalkyl,
unsubstituted or substituted by one or two radicals selected from the group consisting of $C_1$–$C_4$-alkyl, F, amino, $C_1$–$C_3$-alkylamino, $C_1$–$C_3$-dialkylamino, hydroxyl, carboxyl, $C_1$–$C_3$-alkoxy, pyridyl, imidazolyl, thiazolyl, oxazolyl, phenyl, with phenyl being unsubstituted or substituted by one or two radicals selected from the group consisting of F, Cl, Br, amino, $C_1$–$C_3$-alkylamino, $C_1$–$C_3$-dialkylamino, hydroxyl, carboxyl, $C_1$–$C_3$-alkoxy, $C_1$–$C_4$-alkyl;

or a monocyclic, condensed dicyclic or condensed tricyclic aryl radical,
unsubstituted or substituted by one or two radicals selected from the group consisting of $C_1$–$C_4$-alkyl, F, Cl, Br, amino, $C_1$–$C_3$-alkylamino, $C_1$–$C_3$-dialkylamino, hydroxyl, carboxyl, $C_1$–$C_3$-alkoxy;

or a saturated or unsaturated, monocyclic or dicyclic heterocyclic radical, which contains a total of one or two heteroatoms, which can, independently of one another, be N, S or O,
where the radical is unsubstituted or substituted by one or two radicals selected from the group consisting of $C_1$–$C_4$-alkyl, F, amino, $C_1$–$C_3$-alkylamino, $C_1$–$C_3$-dialkylamino, hydroxyl, carboxyl, $C_1$–$C_3$-alkoxy, and also, if the heterocyclic radical is aromatic, Cl and Br.

4. The process as claimed in claim 1, wherein R is as defined below:

$C_1$–$C_6$-alkyl,
unsubstituted or substituted by one or two radicals selected from the group consisting of F, amino, $C_1$–$C_3$-alkylamino, $C_1$–$C_3$-dialkylamino, hydroxyl, carboxyl, $C_1$–$C_3$-alkoxy, $C_3$–$C_8$-cycloalkyl, pyridyl, imidazolyl, thiazolyl, oxazolyl, phenyl, with phenyl being unsubstituted or substituted by one or two radicals selected from the group consisting of F, Cl, Br, $C_1$–$C_3$-alkyl, $C_1$–$C_3$-alkoxy;

or $C_3$–$C_6$-cycloalkyl,
unsubstituted or substituted by one or two radicals selected from the group consisting of $C_1$–$C_4$-alkyl, F, amino, $C_1$–$C_3$-alkylamino, $C_1$–$C_3$-dialkylamino, hydroxyl, carboxyl, $C_1$–$C_3$-alkoxy, pyridyl, imidazolyl, thiazolyl, oxazolyl, phenyl;

or phenyl,
unsubstituted or substituted by one or two radicals selected from the group consisting of $C_1$–$C_3$-alkyl, F, Cl, Br, amino, $C_1$–$C_3$-alkylamino, $C_1$–$C_3$-dialkylamino, hydroxyl, carboxyl, $C_1$–$C_3$-alkoxy;

or an unsaturated monocyclic or dicyclic heterocyclic radical, which contains a total of one or two heretoatoms, which can, independently of one another, be N, S or O,
where the radical is unsubstituted or substituted by one or two radicals selected from the group consisting of $C_1$–$C_3$-alkyl, F, amino, $C_1$–$C_3$-alkylamino, $C_1$–$C_3$-dialkylamino, hydroxyl, carboxyl, $C_1$–$C_3$-alkoxy, and also, if the heterocyclic radical is aromatic, Cl and Br.

5. The process as claimed in claim 1, wherein R is as defined below:

$C_1$–$C_4$-alkyl;
or $C_3$–$C_6$-cycloalkyl;
or phenyl,
unsubstituted or substituted by one or two radicals selected from the group consisting of methyl, F, Cl, Br, amino, $C_1C_3$-alkylamino, $C_1$–$C_3$-dialkylamino, hydroxyl, carboxyl, methoxy;

or pyridyl, imidazolyl, benzimidazolyl, thiazolyl, benzothiazolyl, oxazolyl or benzoxazolyl.

6. The process as claimed in claim 1, wherein the polar aprotic solvent used is N-methylpyrrolidone, N-methylformamide, dimethylformamide, dimethylacetamide, sulfolane, dimethyl sulfoxide, butyrolactone or tetrahydrofuran.

7. The process as claimed in claim 1, wherein the process is carried out at atmospheric pressure or under a pressure of up to 5 bar.

8. A process for preparing trifluoroethyl sulfur compounds from thiolates and 1-chloro-2,2,2-trifluoroethane, which comprises allowing 1-chloro-2,2,2-trifluoroethane to act in a polar aprotic solvent, in absence of a catalyst, upon salts of thiols of the formula RSH, at a low pressure of up to 5 bar, where R is an unsubstituted or substituted radical as defined below:

$C_1$–$C_{20}$-alkyl or $C_3$–$C_{12}$-cycloalkyl or a monocyclic, condensed dicyclic or condensed tricyclic aryl radical, or a saturated or unsaturated monocyclic or dicyclic heterocyclic radical, which contains a total of one or two heteroatoms, which can, independently of one another, he N, S or O.

9. A process for preparing trifluoroethyl sulfur compounds from thiolates and 1-chloro-2,2,2-trifluoroethane, which comprises allowing 1-chloro-2,2,2-trifluoroethane to act in a polar aprotic solvent upon salts of thiols of the formula RSH, at a low pressure up to 5 bar, where R is an unsubstituted or substituted radical as defined below:

$C_1$–$C_{20}$-alkyl or $C_3$–$C_{12}$-cycloalkyl or a monocyclic, condensed dicyclic or condensed tricyclic aryl radical, or a saturated or unsaturated monocyclic or dicyclic heterocyclic radical, which contains a total of one or two heteroatoms, which can, independently of one another, be N, S or O.

10. The process as claimed in claim 9, wherein the process is carried out without the use of a catalyst.

11. The process as claimed in claim 1, wherein the process is carried out without the use of a catalyst.

12. The process as claimed in claim 1, wherein the temperature of a process is from 40° C. to 100° C.

13. The process as claimed in claim 8, wherein the temperature of the reaction is from 40° C. to 100° C.

14. The process as claimed in claim 9, wherein the temperature is carried out from 40° C. to 100° C.

15. The process as claimed in claim 10, wherein the temperature is carried out from 40° C. to 70° C.

16. The process as claimed in claim 11, wherein the temperature is carried out from 40° C. to 60° C.

* * * * *